(12) United States Patent
Kato

(10) Patent No.: US 10,054,554 B2
(45) Date of Patent: Aug. 21, 2018

(54) METHOD FOR EVALUATING SEMICONDUCTOR WAFER

(71) Applicant: SHIN-ETSU HANDOTAI CO., LTD., Tokyo (JP)

(72) Inventor: Masahiro Kato, Takasaki (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/573,058

(22) PCT Filed: Mar. 9, 2016

(86) PCT No.: PCT/JP2016/001274
§ 371 (c)(1),
(2) Date: Nov. 9, 2017

(87) PCT Pub. No.: WO2016/189778
PCT Pub. Date: Dec. 1, 2016

(65) Prior Publication Data
US 2018/0136143 A1   May 17, 2018

(30) Foreign Application Priority Data

May 27, 2015 (JP) ................................. 2015-107398

(51) Int. Cl.
*G01N 21/00* (2006.01)
*G01N 21/95* (2006.01)
*G01N 21/94* (2006.01)

(52) U.S. Cl.
CPC ......... *G01N 21/9501* (2013.01); *G01N 21/94* (2013.01); *G01N 2201/06113* (2013.01)

(58) Field of Classification Search
CPC ............... G01N 21/9501; G01N 21/94; G01N 2201/06113

(Continued)

(56) References Cited

U.S. PATENT DOCUMENTS 6,515,742 B1   2/2003 Ruprecht
6,726,319 B1   4/2004 Yanase et al.
(Continued)

FOREIGN PATENT DOCUMENTS

JP   2009-162768 A   7/2009
JP   2010-129748 A   6/2010
(Continued)

OTHER PUBLICATIONS

May 24, 2016 International Search Report issued in International Patent Application No. PCT/JP2016/001274.

*Primary Examiner* — Tri T Ton
(74) *Attorney, Agent, or Firm* — Oliff PLC

(57) ABSTRACT

A method for evaluating a semiconductor wafer includes detecting semiconductor wafer LPDs as an examination sample in two measurement modes, performing size classification of the LPDs, calculating a distance between detection coordinates and a relative angle in the two measurement modes, presetting determination criteria to determine each LPD as a foreign matter or killer defect in accordance with each classified size, detecting semiconductor wafer LPDs as an evaluation target in the two measurement modes, performing size classification of the LPDs as the evaluation target, calculating a distance between detection coordinates and a relative angle of the evaluation target, and classifying the LPDs detected on a surface of the evaluation target into the killer defect and the foreign mater based on a result of the calculation and the determination criteria. The method enables classifying all LPDs from which quantitative size information cannot be provided, into the killer defect and foreign matter.

16 Claims, 12 Drawing Sheets

(58) Field of Classification Search
USPC ..... 356/237.1–237.6, 239.1–239.8, 600–613
See application file for complete search history.

(56) References Cited

U.S. PATENT DOCUMENTS

2003/0210393 A1 11/2003 Vaez-Iravani et al.
2009/0040512 A1 2/2009 Nabeshima et al.

FOREIGN PATENT DOCUMENTS

| JP | 2011-249479 A | 12/2011 |
| WO | 01/27600 A1 | 4/2001 |
| WO | 2005/101483 A1 | 10/2005 |

METHOD FOR EVALUATING SEMICONDUCTOR WAFER

TECHNICAL FIELD

The present invention relates to a method for evaluating a semiconductor wafer.

BACKGROUND ART

In a device manufacturing process using a semiconductor wafer, various kinds of processing, e.g., polishing, film production, etching, ion implantation, cleaning, a heat treatment, exposure, coating, and bonding are performed to a silicon wafer which is a material. A defect is produced during a plurality of such processes in some situation, and it degrades quality of a final product but also adversely affects subsequent processes in some cases. The defect which affects the quality or the processes is called a killer defect, and a wafer in which even one killer defect is produced may be determined to be a defective product as a whole. In a case where the wafer becomes a defective product after subsequent processes due to a killer defect produced in an initial process in particular, costs concerning the subsequent processes are all lost.

To avoid such a situation, a wafer containing a killer defect is sorted out at a halfway stage. In general, a sorting method using a laser surface inspection apparatus is adopted, and there are, e.g., SP1, SP2, and SP3 manufactured by KLA-Tencor Corporation as the apparatus. These apparatuses detect scattering light from a defect, can perform high-speed processing, and have characteristics of high sensitivity.

On the other hand, on a wafer surface, there are killer defects as well as foreign matters adhering to the surface. Since they can be easily removed by subsequent cleaning, their influence on final quality of the wafer is slight, but discrimination from the killer defects cannot be effected in a halfway inspection using the laser surface inspection apparatus, which may lead to false recognition as defects. This case corresponds to overkill, and a loss as a material is produced. Thus, in the inspection conducted during a halfway process, highly accurately discriminating between the killer defects and the foreign matters is important. Although there is an inspection method for performing highly accurate discrimination by direct observation of high magnification, there is generally a limit in processing speed, and an inspection frequency is restricted.

Thus, as a method for improving a classification accuracy of an LPD (Light Point Defect) which is detected by the laser surface inspection apparatus, a distribution method using a plurality of pieces of detection angle information has been suggested. A surface is irradiated with a laser beam from an obliquely upper direction while scanning a wafer, detection of a signal of light which scatters in a high-angle direction is determined as DNO (low-angle incidence/high-angle detection), detection of a signal of light which scatters in a low-angle direction is determined as DWO (low-angle incidence, low-angle detection), and respective calculated LPD sizes are compared with each other, thereby performing classification. It is to be noted that D is an initial of Darkfield, and it means dark field inspection.

For example, Patent Document 1 discloses a method for classifying a particle and a microscratch by using an LPD size ratio of DWO and DNO. Patent Document 2 discloses that a crystal defect and a foreign matter are classified by using an LPD size ratio of DWO and DNO. Patent Document 3 discloses that a pit and a protrusion are classified by using an LPD size ratio of DWO and DNO. Patent Document 4 discloses that a defect and a foreign matter are classified by using an LPD size ratio of DWO and DNO.

CITATION LIST

Patent Literatures

Patent Document 1: Japanese Unexamined Patent Application Publication (Kokai) No. 2009-162768
Patent Document 2: Japanese Unexamined Patent Application Publication (Kokai) No. 2010-129748
Patent Document 3: Japanese Unexamined Patent Application Publication (Kokai) No. 2011-249479
Patent Document 4: International Publication No. WO2005/101483

DISCLOSURE OF INVENTION

Problem to be Solved by the Invention

Although the above-described methods are a determination method based on the LPD size information of the DWO and the DNO, when an actual LPD size is large and scattering intensity exceeds a saturation range of a detector, a problem that quantitative size information cannot be obtained arises. This state will now be described with reference to FIG. 11. FIG. 11 is a view showing a relationship between an actual LPD size and detection light signal intensity of an LPD. Five typical detection signal examples are aligned on an axis of abscissa, and an axis of ordinate represents scattering intensity (signal intensity) of detected light. Signal Examples 1 to 3 in FIG. 11 show examples where the LPD size can be quantified. In the laser surface inspection apparatus, a high-sensitivity detector is used, and slight light scatters during scanning a normal surface. When a laser beam strikes on an LPD, spike-like intensive scattering signal is detected, and an LPD size is calculated from peak intensity of signal which is beyond a set lower limit threshold value. For this calculation, a conversion expression which is derived from a size of a PSL (polystyrene latex) standard particle and an actually measured value of the scattering intensity thereof is used. However, the detector has an upper limit value which enables quantification of intensity, and the LPD size cannot be quantified when this value is exceeded. Signal Example 4 in FIG. 11 shows this state. Detected signal intensity is saturated at the intensity upper limit, and intensity exceeding this limit cannot be identified as a numerical value even if an actual LPD size has a difference. It is to be noted that, when an actual LPD size is large and a duration time of a saturated signal is longer than a fixed scanning width like Signal Example 5 in FIG. 11, a width of the duration time can be expressed as a numeral value as an area by integration. In this manner, Signal Examples 1 to 3 and Signal Example 5 in FIG. 11 can be converted into numeral values, but a problem that numerical value information of a size cannot be obtained arises in Signal Example 4. Patent Documents 1 to 3 requires numerical value information of LPD sizes provided by both the DWO and the DNO, and a problem that a killer defect and a foreign matter cannot be discriminated arises if one of them corresponds Signal Example 4 in FIG. 11. In particular, the killer defect which considerably affects quality has a large size and often corresponds to this problem.

It is to be noted that, in FIG. 11 and a description of the present invention, an LPD detected by a signal like those of Signal Examples 1 to 3 will be referred to as a size LPD, an LPD detected by a signal like that of Signal Example 4 will be referred to as a saturation LPD, and an LPD detected by a signal like that of Signal Example 5 will be referred to as an area LPD.

In view of the problem, it is an object of the present invention to provide an evaluation method of a semiconductor wafer which enables sorting a killer defect and a foreign matter from all LPDs including a saturation LPD from which quantitative size information cannot be obtained.

Means for Solving Problem

To achieve the object, the present invention provides a method for evaluating a semiconductor wafer by which LPDs on a surface of a semiconductor wafer are detected with the use of a laser surface inspection apparatus and the detected LPDs are classified into a crystal defect on the surface of the semiconductor wafer and a foreign matter on the surface of the semiconductor wafer, including steps of:

detecting the LPDs on the surface of a semiconductor wafer as an examination sample in two measurement modes of the laser surface inspection apparatus, the two measurement modes consisting of low-angle incidence/low-angle detection (DWO) and low-angle incidence/high-angle detection (DNO);

performing size classification based on size information of the LPDs detected in the two measurement modes;

calculating, from detection coordinates of each LPD detected in the two measurement modes, a distance between the detection coordinates and a relative angle to a wafer center in the two measurement modes;

presetting, in accordance with each classified size, determination criteria to determine each LPD having the distance between the detection coordinates and the relative angle in the two measurement modes which fall within a predetermined range as a foreign matter and to determine any LPD other than the LPD falling in the predetermined range as a killer defect which is a defect of the semiconductor wafer as an examination sample;

detecting the LPDs of a semiconductor wafer as an evaluation target in the two measurement modes;

performing size classification based on size information of the LPDs detected in the two measurement modes as to the semiconductor wafer as the evaluation target;

calculating, from detection coordinates of each LPD detected in the two measurement modes, a distance between the detection coordinates and a relative angle to a wafer center in the two measurement modes as to the semiconductor wafer as the evaluation target; and classifying the LPDs detected on a surface of the semiconductor as the evaluation target into the killer defect and the foreign matter based on a result of the calculation and the determination criteria.

According to such a method for evaluating a wafer, since the coordinate information of each LPD provided by the DWO and the DNO is adopted in addition to the size information of each LPD provided by the DWO and the DNO, the killer defect and the foreign matter can be sorted (discriminated) from all LPDs including the saturation LPD from which the quantitative size information cannot be obtained.

Further, in the present invention, the semiconductor wafer as the examination sample and the semiconductor wafer as the evaluation target can be epitaxial wafers.

The inventive method for evaluating a wafer can be preferably used for evaluation of the epitaxial wafer in which an epitaxial defect (which will be also referred to as an epi-defect hereinafter) which is a kind of killer defect may be produced.

Furthermore, the semiconductor wafer as the evaluation target can be used as a material of a silicon-on-insulator wafer (an SOI wafer).

When the wafer evaluated by the present invention is used as the material of the SOI wafer, a void defect in the SOI wafer can be prevented from being produced.

Moreover, the killer defect can be an epitaxial defect having a square pyramid shape.

Such a defect is apt to produce a difference in signal intensity relative to the detectors of a high angle and a low angle, and also apt to produce a difference in detection coordinates. Additionally, it is often the case that such a defect has the high scattering intensity and exceeds a quantification limit of the detectors. In such a case, quantitative intensity information cannot be obtained, and classification using positional information (coordinate information) is rather effective. Thus, the present invention which uses the coordinate information of the LPD provided by the DWO and the DNO is particularly effective.

Further, it is preferable, at the time of setting the determination criteria, to confirm whether the detected LPD is the killer defect with the use of an evaluation method different from the evaluation method using the DWO and the DNO.

According to such a method for evaluating a wafer, the determination criteria can be further accurately set.

Effect of the Invention

According to the present invention, a killer defect and a foreign matter can be easily and highly accurately sorted from all LPDs including the saturation LPD from which the quantitative size information cannot be provided in the laser surface inspection apparatus, and overall losses including a failure loss in a subsequent process and a loss of a material wafer can be suppressed.

BEST MODE(S) FOR CARRYING OUT THE INVENTION

The present invention will now be described hereinafter in detail.

As described above, there has been demanded a method for evaluating a semiconductor wafer which enables soring a killer defect and a foreign matter from all LPDs including a saturation LPD from which quantitative size information cannot be obtained.

To achieve the object, the present inventor conducted the earnest examinations. As a result, the present inventor has found out that the method for evaluating a wafer which utilizes coordinate information of an LPD provided by DWO and DNO in addition to size information of the LPD provided by the DWO and the DNO can solve the problem, thereby bringing the present invention to completion.

Although an embodiment according to the present invention will now be specifically described hereinafter, the present invention is not restricted thereto.

Figure 1:
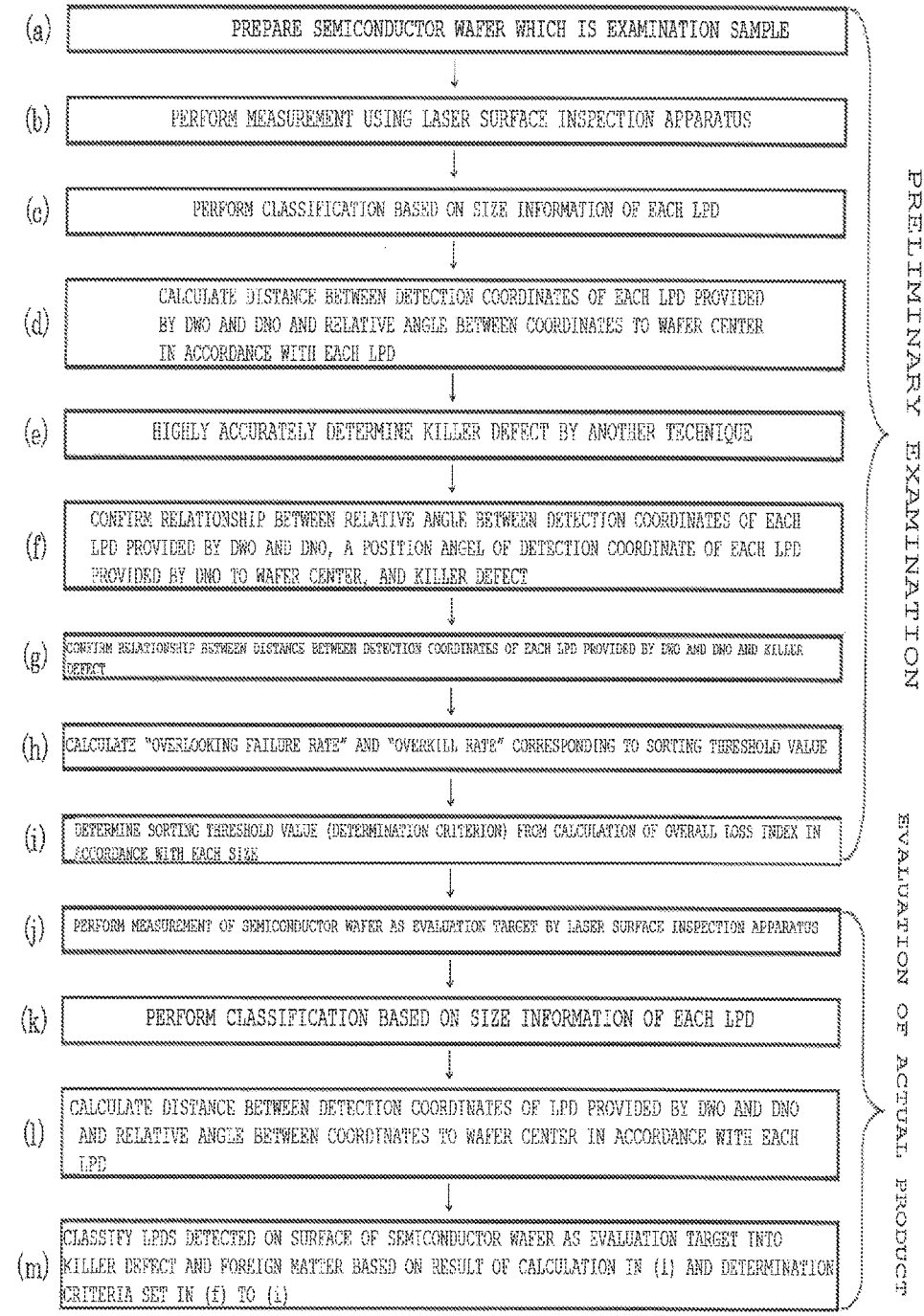
FIG. 1 is a flowchart showing an example of an inventive method for evaluating a semiconductor wafer.

FIG. 1 is a flowchart showing an example of the method for evaluating a semiconductor wafer according to the present invention, and specific contents of each item will be described below. It is to be noted that a semiconductor wafer which is an evaluation target here is regarded as a material in a subsequent process, and the following procedure (FIG. 1(a) to (i)) is intended to set determination criteria on availability of this wafer. The semiconductor wafer as the evaluation target is evaluated based on the determination criteria (FIG. 1(j) to (m)).

First, a sample for preliminary examination (a semiconductor wafer which is an examination sample) is prepared (FIG. 1(a)). Although a type of the semiconductor wafer which is the examination sample is not restricted in particular, it can be an epitaxial wafer. The present invention can be preferably used for evaluation of an epitaxial wafer in which an epi-defect which is a kind of killer defect is produced in some situations.

Then, the target sample is measured by using a laser surface inspection apparatus (FIG. 1(b)). Specifically, LPDs on a surface of the semiconductor wafer which is the examination sample are detected in two measurement modes, i.e., low-angle incidence/low-angle detection (DWO) and low-angle incidence/high-angle detection (DNO).

As the laser surface inspection apparatus used in this example, one having the two measurement modes can suffice. Thus, one provided with an incidence system having at least one type of incidence angle and a detection system having two types of detection angles can suffice. In this case, incidence at the one type of incidence angle is low-angle incidence having an incidence angle which is a predetermined angle (e.g., 30°) or less, and detection at a higher one of the two types of detection angles is high-angle detection whilst detection at the other is low-angle detection.

Figure 2:
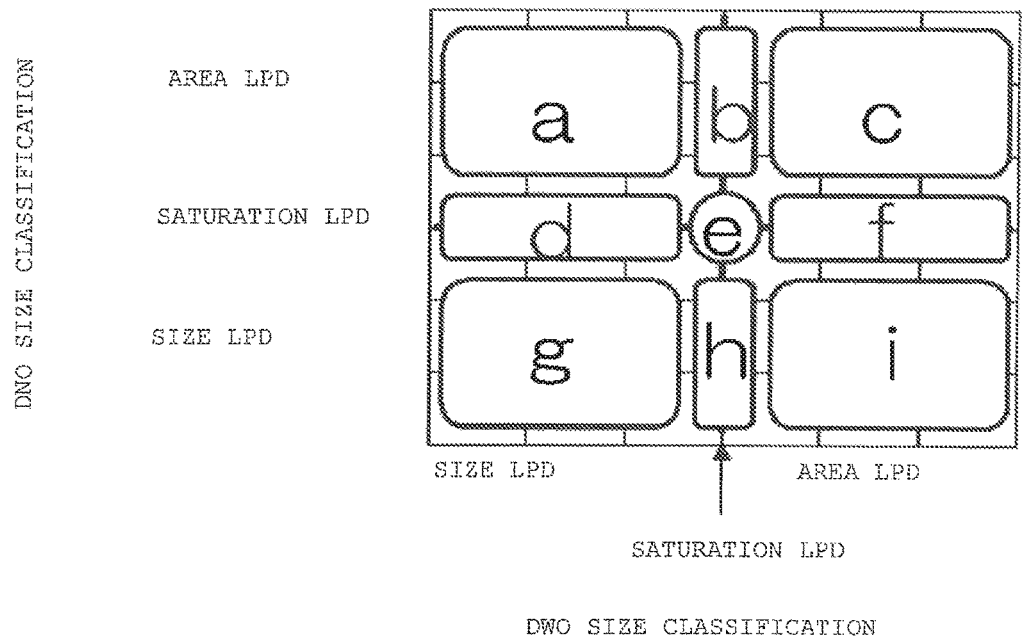
FIG. 2 is a view showing an example of region classification based on LPD sizes provided by DWO and DNO.

Size classification is performed based on size information of each LPD detected in the two measurement modes (FIG. 1(c)). Specifically, size information of each LPD provided by the DWO and the DNO is confirmed with respect to all LPDs detected in FIG. 1(b), and the LPDs are divided into nine regions shown in FIG. 2. FIG. 2 is a view showing an example of region classification according to the sizes of the LPDs provided by the DWO and the DNO. An axis of ordinate represents an LPD size provided by the DNO, and an axis of abscissa represents an LPD size provided by DWO. An LPD which is detected by either the DWO or DNO alone is determined to be exempt from a killer defect determination.

Figure 3:
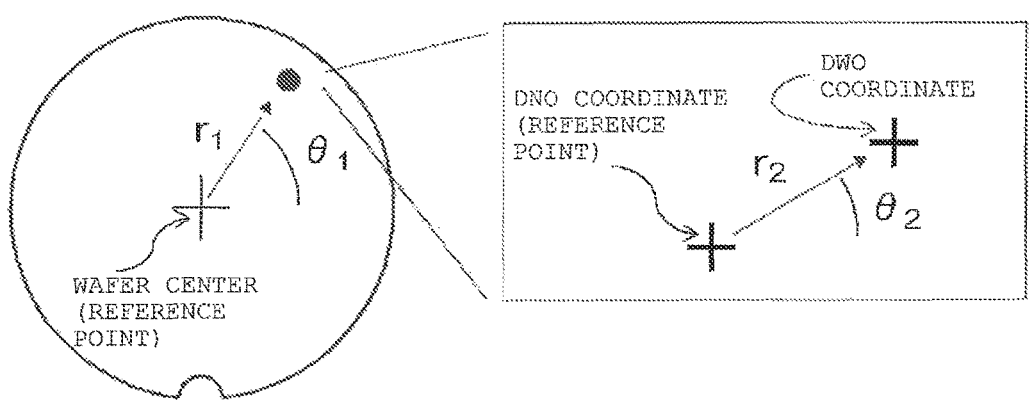
FIG. 3 is a view for explaining a distance between detection coordinates and a relative angle of an LPD provided by the DWO and the DNO.

Then, as to all the LPDs detected in FIG. 1(b), a distance between detection coordinates and a relative angle to a wafer center of each LPD provided by the DWO and the DNO are calculated (FIG. 1(d)). Based on the measurement in FIG. 1(b), coordinate information of each LPD can be acquired in two measurement modes. As to each LPD, a distance between the detection coordinates and a relative angle in the two measurement modes are calculated by using this information. FIG. 3 shows an example. FIG. 3 is a view for explaining a distance between detection coordinates and a relative angle of each LPD provided by the DWO and the DNO. In the example of FIG. 3, a difference between the detection coordinates of the LPD provided by the DWO and the DNO is represented as a polar coordinate which uses a distance $r_2$ and a relative angle $\theta_2$ to the detection coordinate of the LPD provided by the DWO when the detection coordinate of the LPD provided by the DNO is determined as a reference point. Here, a radial position is also calculated. The radial position is represented as a polar coordinate using a distance $r_1$ and a position angle $\theta_1$ to the detection coordinate of the LPD provided by the DNO when the wafer center is determined as an origin.

Then, determination criteria which determine an LPD whose distance between detection coordinates and whose relative angle in the two measurement modes fall within a predetermined range as a foreign matter and also determine any other LPD than the LPD falling in the predetermined range as a killer defect which is a defect of the semiconductor wafer are preset in accordance with each classified size.

At this time, it is preferable to confirm whether a detected LPD is a killer defect by an evaluation method different from the evaluation method using the DWO and the DNO, especially a different evaluation method having a high determination accuracy (FIG. 1(e)). As an example of the different evaluation method, a method using an LPD image obtained by a bright field examination apparatus, a method for conducting a test in a post-process and determining a killer defect corresponding to a failure producing position, or the like can be considered. Consequently, the determination criteria can be further accurately set.

The determination criteria can be set by, e.g., FIG. 1(f) to (i) described below. It is to be noted that a type of the a killer defect is not restricted in particular, but it can be, e.g., a square-pyramid-shaped epitaxial defect. That is because quantitative intensity information of such a defect is not obtained by the laser surface inspection apparatus in some situations, and sorting using the coordinate information is effective.

Figure 4:
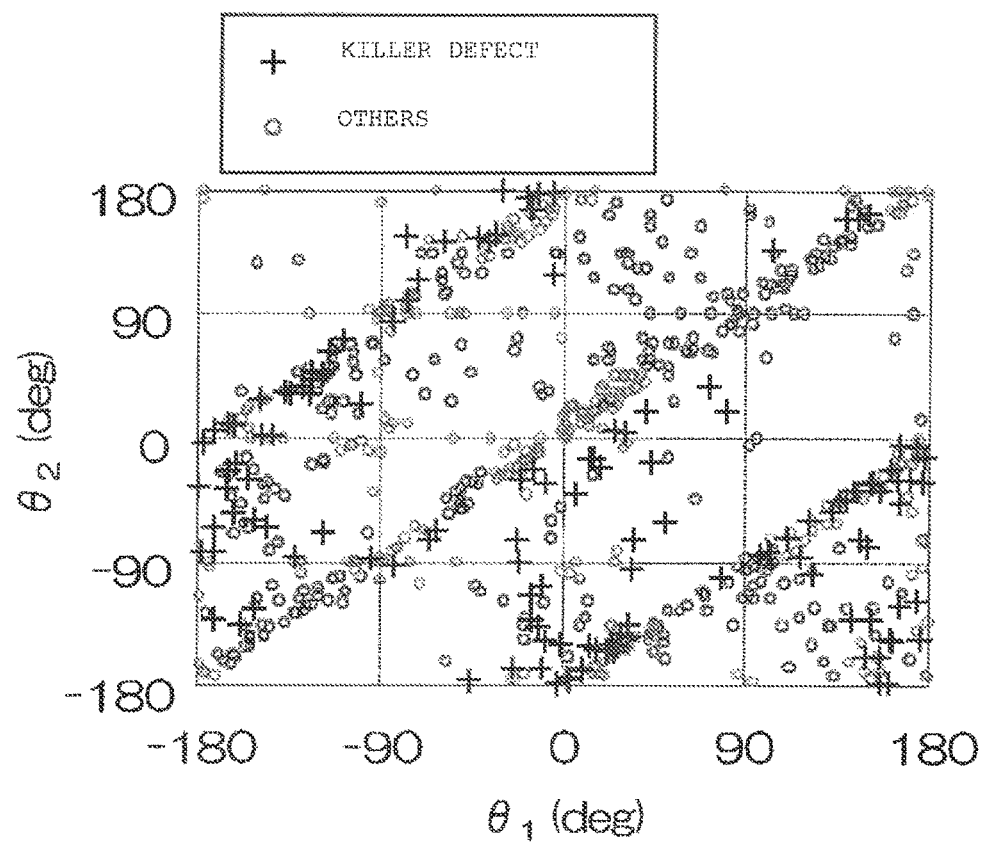
FIG. 4 is a graph showing a relationship between a relative angle $\theta_2$ of a detection coordinate of an LPD provided by the DWO to a detection coordinate of the LPD provided by the DNO, a position angle $\theta_1$ of the LPD provided by the DNO to a wafer center, and applicability of a killer defect.
Figure 5:
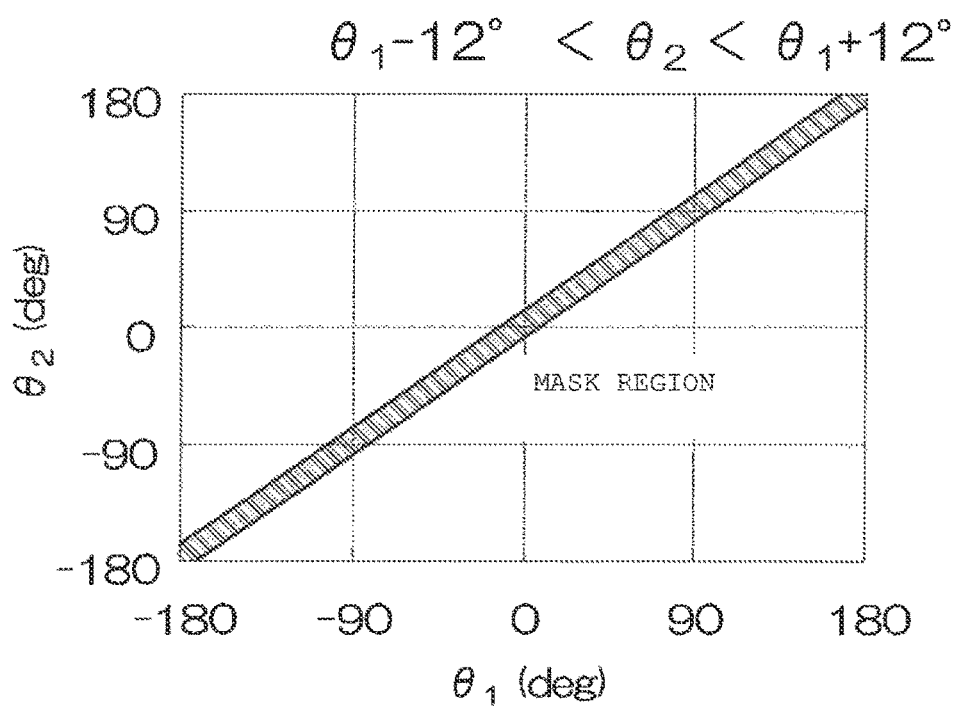
FIG. 5 is a graph showing a mask region which is set based on the relationship in FIG. 4.

First, the relationship between the relative angle $\theta_2$ of the detection coordinate of the LPD provided by the DWO relative to the detection coordinate of the LPD provided by the DNO, the position angle $\theta_1$ of the detection coordinate of the LPD provided by the DNO relative to the wafer center, and applicability of the killer defect obtained in FIG. 1(d) is confirmed in each of the nine regions in FIG. 2 (FIG. 1(f)). FIG. 4 shows an example. Further, FIG. 5 shows a mask region set based on the relationship in FIG. 4. Each LPD corresponding to the killer defect in FIG. 4 has a generation frequency lowered in a masked $\theta$ region shown in FIG. 5. In such a case, a determination criterion to determine each LPD corresponding to the mask region to be acceptable (i.e., a foreign matter) is set. In the example of FIG. 5, a range of $\theta_1-12°<\theta_2<\theta_1+12°$ is determined as a mask region.

Figure 6:
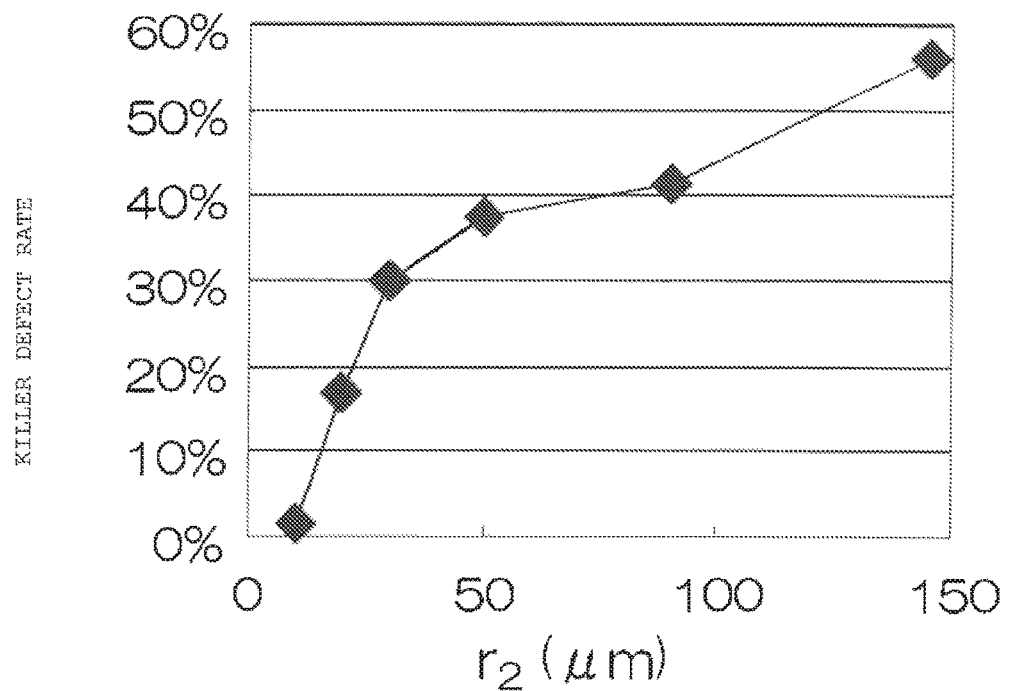
FIG. 6 is a graph showing an example of a relationship between a distance $r_2$ between the detection coordinates of the LPD provided by the DWO and the DNO and an applicability rate of the killer defect.

Then, the relationship between the distance $r_2$ between the detection coordinates of the LPD provided by the DWO and the DNO and the applicability rate of the killer defect obtained in FIG. 1(d) is confirmed in each of the nine regions in FIG. 2 (FIG. 1(g)). FIG. 6 shows its example, and the applicability rate of the killer defect rises as the distance $r_2$ between the detection coordinates of the LPD provided by the DWO and the DNO increases. In such a case, a fixed sorting threshold value is set to $r_2$, and a determination criterion to determine each LPD which is equal to or higher than this threshold value to be rejected (i.e., a killer defect) is adopted.

Figure 7:
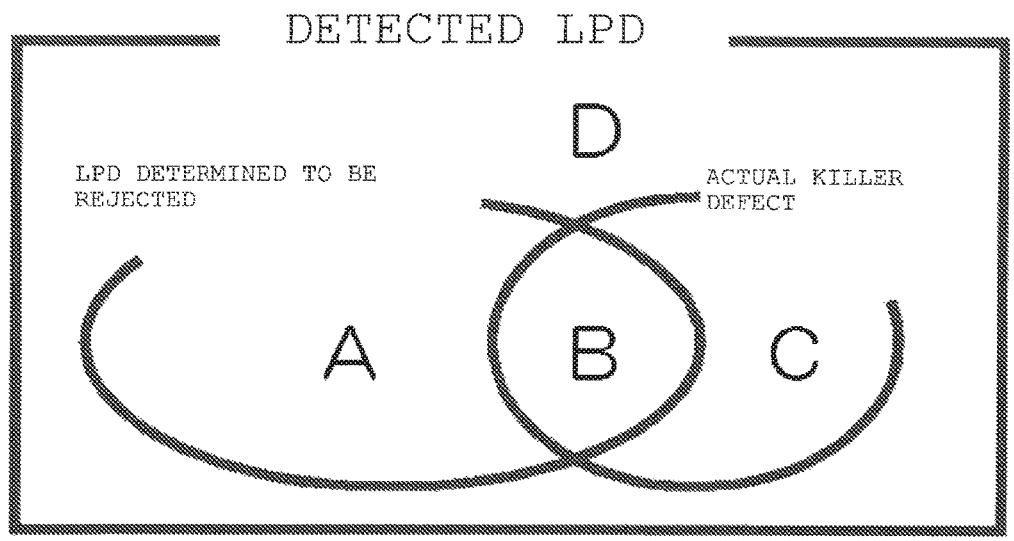
FIG. 7 is a view showing concepts of an "overlooking failure rate" and an "overkill rate"
Figure 8:
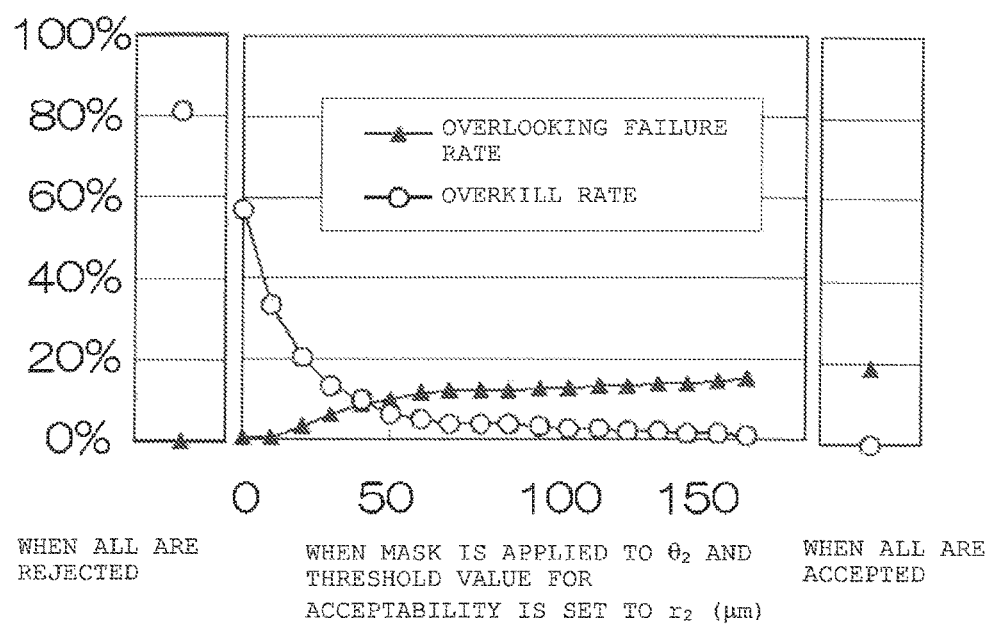
FIG. 8 is a graph showing a relationship between the distance $r_2$ between the detection coordinates of the LPD provided by the DWO and the DNO and both the "overlooking failure rate" and the "overkill rate"

Subsequently, an "overlooking failure rate" and an "overkill rate" when the determination criteria are used are calculated in each of the nine regions in FIG. 2 (FIG. 1(h)). FIG. 7 shows each concept. Two ellipses are drawn, and a left ellipse represents a set of LPDs which are rejected by a result of the laser surface inspection apparatus based on one or both of the determination criteria in FIG. 1(f) and FIG. 1(g). On the other hand, a right ellipse represents a set of killer defects. When the two ellipses perfectly coincide with each other, since the killer defects can be perfectly sorted out, this is the most ideal state, but the two ellipses do not overlap in reality, and a deviation is produced. Consequently, four types of sets can be assumed, and they are shown as A to D in the drawing. In a set of A is a set in which LPDs are not actually the killer defects but they are rejected and correspond to "overkill defects". Since a wafer which is supposed to be acceptable cannot be used, a material loss is produced. In a set of B, the killer defects are correctly determined to be rejected, and an unnecessary loss is not produced. In a set of C, LPDs correspond to "overlooking defects" which are actually the killer defects but determined to be acceptable. Since a failure is produced in a subsequent process, a loss due to the failure is generated. In a region of D, each foreign matter which does not have an adverse influence is determined to be acceptable as it is, and no loss is produced. The unnecessary loss is produced by the two sets, i.e., A and C, and a value provided by dividing the number of respective corresponding LPDs by the number of populations (A+B+C++D) is defined as the "overkill rate" or the "overlooking failure rate". Each value varies depending on the determination criteria in FIG. 1(f) and FIG. 1(g), and the distance $r_2$ between the detection coordinates of each LPD provided by the DWO and the DNO in FIG. 1(g) continuously varies in correspondence with the setting of the sorting threshold value. FIG. 8 shows a calculation example of the "overkill rate" and the "overlooking failure rate". FIG. 8 is a graph showing a relationship between the distance $r_2$ between the detection coordinates of each LPD provided by the DWO and the DNO, the "overlooking failure rate", and the "overkill rate". Data at a left end represents a case where all detected LPDs are rejected and, in this case, the "overlooking failure rate" is 0%, but the "overkill rate" increases.

Contrarily, data at a right end represents a case where all detected LPDs are determined to acceptable, and the "overkill rate" is 0%, but the "overlooking failure rate" increases. A graph at the center is a graph in a case where the mask of $\theta$ provided in FIG. 1(f) is applied and the threshold value for the distance $r_2$ between the detection coordinates of each LPD provided by the DWO and the DNO calculated in FIG. 1(g) is continuously changed, and the "overkill rate" and the "overlooking failure rate" continuously vary.

Then, an overall loss index is calculated in each of the nine regions in FIG. 2, and determination conditions under which this value becomes minimum are set in accordance with each region (FIG. 1(i)). The overall loss index can be provided by the following Expression (1).

Overall loss index=Overlooking failure rate×Product value coefficient+Overkill rate×material value coefficient  (1)

(wherein the overlooking failure rate and the overkill rate are as described above, the product value coefficient is a coefficient determined in correspondence with a product value, and the material value coefficient is a coefficient determined in correspondence with a material value.)

Figure 9:
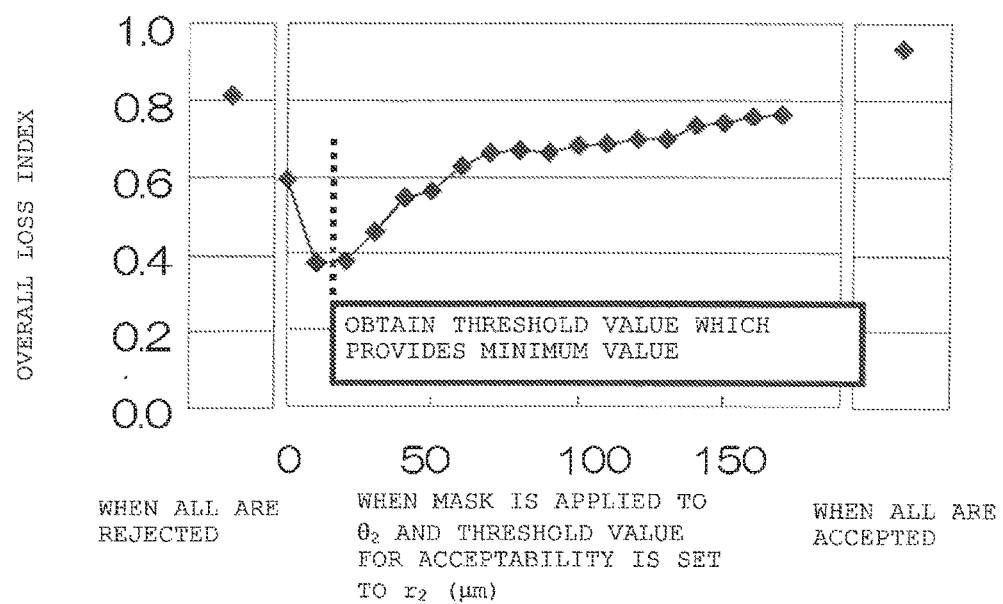
FIG. 9 is a graph showing a relationship between the distance $r_2$ between the detection coordinates of the LPD provided by the DWO and the DNO and an overall loss index.

FIG. 9 shows a calculation example (a specific example of a determination method) of the overall loss index. FIG. 9 is a graph showing a relationship between the distance $r_2$ between the detection coordinates of each LPD provided by the DWO and the DNO and the overall loss index. Like FIG. 8, data at a left end in FIG. 9 represents a case where all detected LPDs are rejected, data at a right end represents a case where all detected LPDs are accepted, and a graph at the center is a graph when the mask of $\theta$ provided in FIG. 1(f) is applied and the threshold value for the distance $r_2$ between the detection coordinates of each LPD provided by the DWO and the DNO calculated in FIG. 1(g) is continuously changed.

A final loss is calculated by integrating both a material loss produced due to the "overkill" and a failure loss in a subsequent process produced due to the "overlooking failure". At that time, since there is a difference between the material value and the later product value, a value coefficient considering an influence is multiplied by each failure rate. FIG. 9 shows a calculation example when the "material value coefficient"=1 and the "product value coefficient"=5, and a sum total of values provided by multiplying these coefficient by the "overkill rate" and the "overlooking failure rate" in FIG. 8 becomes the overall loss index. In the example of FIG. 9, the overall loss index when the sorting threshold value of the $r_2$ value is set to 10 to 20 μm is minimum. The thus obtained sorting threshold value is adopted as a determination criterion of each corresponding region in FIG. 2. Likewise, the determination criterion is set in accordance with each classified size.

Then, the determination criteria set in FIG. 1(f) to (i) are applied to a wafer which is in an actual process as an examination target, and LPDs are sorted. Specifically, the LPDs can be sorted based on the following FIG. 1(j) to (m).

It is to be noted that, as the semiconductor wafer as an evaluation target, one which is the same type as the semiconductor wafer as the examination sample can suffice and, for example, an epitaxial wafer can be adopted. Further, such a semiconductor wafer as an evaluation target can be used as a material of an SOI wafer. When the wafer evaluated by the present invention is used as a material of the SOI wafer, generation of void defects in the SOI wafer can be suppressed.

First, LPDs on the semiconductor wafer as an evaluation target are detected in the two measurement modes (FIG. 1(j)).

Then, as to the semiconductor wafer as the evaluation target, size classification is performed based on size information of the LPDs detected in the two measurement modes (FIG. 1(k)).

Subsequently, as to the semiconductor wafer as the evaluation target, a distance between detection coordinates and a relative angle to a wafer center in the two measurement modes are calculated from the detection coordinates of each LPD detected in the two measurement modes (FIG. 1(l)).

In this manner, based on FIG. 1(j) to (l), the laser surface inspection is performed to the wafer which is in an actual process as an examination target like FIG. 1(b) to FIG. 1(d), and the size information and difference information of the coordinates of each LPD provided by the DWO and the DNO are acquired. Furthermore, the respective LPDs are classified into to the nine regions in FIG. 2 based on the acquired size information of the respective LPDs.

Then, based on a result of the calculation in FIG. 1(l) and the determination criteria set in FIG. 1(f) to (i), the LPDs detected on the surface of the semiconductor wafer as the evaluation target are classified into the killer defect and the foreign matter (FIG. 1(m)). Specifically, acceptance of the respective regions in FIG. 2 on the semiconductor wafer as the evaluation target is determined based on the determination criteria (the determination criteria set in accordance with each classified size) determined in FIG. 1(f) to (i). Only a wafer which does not have any rejected LPD (the killer defect) is accepted (namely, evaluated as a wafer having no killer defect), and it is used as a material for a subsequent process.

In the laser surface inspection apparatus, high-speed scanning is performed while irradiating the wafer surface with a laser beam, and scattering light emitted from a foreign matter or a defect present on the surface is detected, thereby acquiring coordinate information or size information of this LPD. At that time, there is adopted a method for setting a plurality of detectors at different detection angle positions and comparing signal intensities from the detectors to discriminate a defect or a foreign matter. This method uses a phenomenon that a scattering direction of light is biased depending on a shape of the defect or the foreign matter. In the present invention, the LPD types are discriminated by using the signal intensities provided from the plurality of detectors as well as the difference information of the coordinates. This method is particularly effective when a shape of a target killer defect has characteristics of a square pyramid shape whose side length is approximately 100 to 200 μm and whose height is approximately 0.2 to 2 μm. Scattering at a wide angle occurs at a top portion of the defect and, on the other hand, scattering at a narrow angle close to a regular reflection angle occurs at a bottom portion of the square pyramid. As a result, a difference in signal intensity is produced between the high-angle detector and the low-angle detector, and a difference in detection coordinate due to a difference in horizontal distance between the top portion and the bottom portion is also produced. The defect having such characteristics in its shape has strong scattering intensity, and the scattering intensity often exceeds a quantification limit of each detector. In such a case, quantitative intensity information cannot be provided, and classification based on the coordinate information is rather effective. It is to be noted that the shape of the defect to which the present invention can be applied is not restricted to the square pyramid shape described in the foregoing example, and the present invention is effective to any defect as long as it is a defect which has an anisotropic aspect in which crystallinity of silicon is reflected and has a size of hundreds of microns in a horizontal direction.

EXAMPLES

Although the present invention will now be more specifically described hereinafter with reference to an example and comparative examples, the present invention is not restricted to the following examples.

A target manufacturing process is a manufacturing process of a silicon-on-insulator (SOI) wafer. Contents of this process are as follows. First, hydrogen ions are implanted into a material wafer (a silicon single crystal wafer) called a bond wafer having an oxide film formed thereon to form a fragile layer, then it is bonded to another material wafer called a base wafer, heat is applied to delaminate a part of the bond wafer, and transference to the base wafer is performed. Subsequently, a bonding heat treatment, a flattening treatment, a sacrificial oxidation treatment, and the like are carried out to provide an SOI wafer product. It is often the case that a polished wafer having a polished surface (a silicon single crystal wafer) is used as a base wafer material of the SOI wafer, and a product using an epitaxial wafer as its material is a target in this example. In the epitaxial wafer, a silicon layer is additionally grown by vapor phase epitaxial growth.

In the epitaxial wafer, a square-pyramid-shaped defect (an epi-defect) whose side length is approximately 100 to 200 μm and whose height is approximately 0.2 to 2 μm is produced in a manufacturing process in some situations. This defect functions as a bonding inhibition factor in a bonding process, and produces an unbonded region called a void defect. In the final SOI product, when one or more void defects which exceed a fixed size are present, the entire wafer is considered to be defective, and hence the epi-defect is regarded as a critical killer defect.

In the current example and comparative examples, killer defects were sorted from the epitaxial wafer as a material by using SP2 manufactured by KLA Tencor Corporation.

Example 1

First, in accordance with FIG. 1(a) to (b), an epitaxial wafer for preliminary examination was prepared, and measurement was carried out by the SP2. A laser was applied from an obliquely upper side, and size information and coordinate information of each LPD provided by a high-angle scattering signal (DNO) and a low-angle scattering signal (DWO) were acquired. Further, all detected LPDs were classified into the nine size regions shown in FIG. 2 in accordance with FIG. 1(c). Furthermore, in accordance with FIG. 1(d), a distance between detection coordinates and a relative angle of each LPD in the two measurement modes were calculated.

Subsequently, based on FIG. 1(e), a highly accurate determination of the killer defect was carried out. A bright field examination apparatus (M350) manufactured by Lasertec Corporation was used for the determination. Since this apparatus can perform detection of LPDs as well as acquisition of images, LPDs can be highly accurately classified. It is to be noted that this technique has a limit in throughput, and hence continuously using it for the purpose of examination of a large amount is difficult, but it is suitable for preliminary examination for a restricted amount.

Subsequently, based on FIG. 1(f) to (i), a sorting threshold value based on the difference information of coordinates of each LPD provided by the DWO and the DNO was determined in each of the nine regions in FIG. 2. Of these nine regions, an overall loss index of the region "h" in FIG. 2 was calculated, and a result shown in FIG. 9 was provided. Consequently, as to the region "h" in FIG. 2, a sorting threshold value for a distance $r_2$ between detection coordinates of each LPD provided by the DWO and the DNO was set to 15 μm, and a determination criterion to determine each LPD having a relative angle $\theta_2$ falling in a range of $\theta_1-120<\theta_2<\theta_1+12°$ to be acceptable was set.

Figure 12:
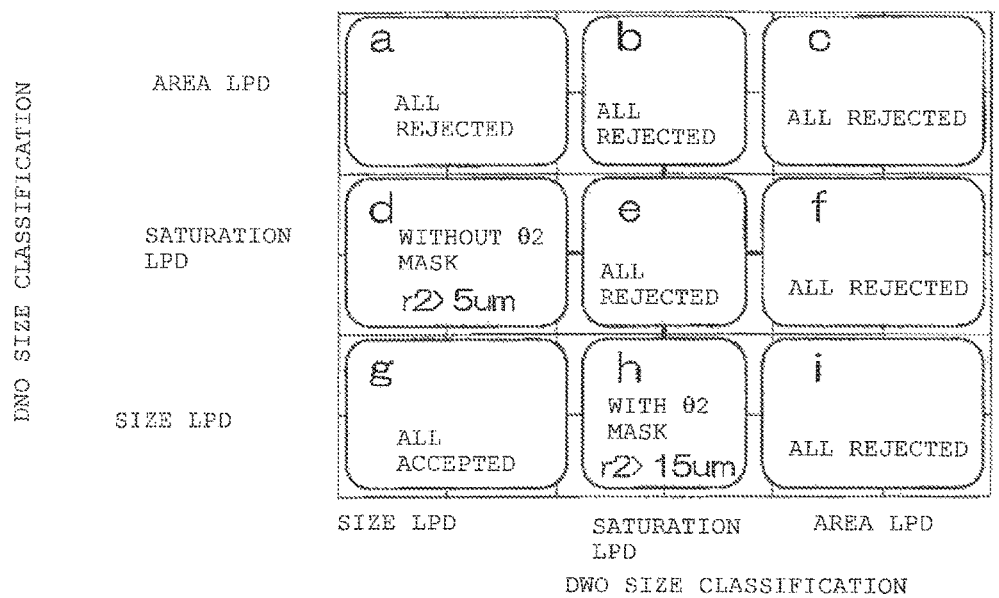
FIG. 12 is a view showing determination criteria of each region in Example 1.

Likewise, determination criteria were set to the regions other than the region "h" in FIG. 2. FIG. 12 shows the determination criteria for the respective regions in Example 1. It is to be noted that each numerical value in FIG. 12 shows a sorting threshold value of $r_2$.

Then, new other 5000 epitaxial wafers were prepared, acceptability was determined in units of wafer based on FIG. 1(j) to (m), and the accepted wafers alone were fed a subsequent SOI manufacturing process.

When SOI wafer products were brought to completion, final losses were examined. As a method for verifying a loss index, material wafers rejected in FIG. 1(m) were reexamined, a value provided by dividing the number of wafers having no killer defect by a total number of original epitaxial wafers was determined as an "overkill rate", and a value provided by multiplying this rate by a material value coefficient was determined as a "material loss index". On the other hand, a value provided by dividing the number of wafers having void failures due to epi-defects in the wafers which were accepted in FIG. 1(m) and were fed to the subsequent process by the total number of original epitaxial wafers was determined as an "overlooking failure rate", and a value provided by multiplying this rate by a product value coefficient was determined as a "failure loss index". At last, a value provided by adding the "material loss index" and the "failure loss index" was determined as an "overall loss index".

Comparative Example 1

5000 epitaxial wafers for comparative examination which are expected to have the same quality as that in Example 1 were prepared, and measurement was carried out by the SP2 based on FIG. 1(b) like Example 1. A laser was applied from an obliquely upper side, and size information of each LPD provided by a high-angle scattering signal (DNO) and a low-angle scattering signal (DWO) was acquired. Moreover, all detected LPDs were classified into the nine size regions shown in FIG. 2 based on FIG. 1(c). All these epitaxial wafers were fed to a subsequent SOI manufacturing process.

When SOT wafer products were brought to completion, final losses were examined. A value provided by dividing the number of the SOI wafer products having void failures due to epi-defects by the total number of original epitaxial wafers was determined as an "overlooking failure rate", and a value provided by multiplying this rate by a product value coefficient was determined as a "failure loss index". In this case, since all the epitaxial wafers were used as a material, the "material loss index" was zero, and the "overall loss index"=the "failure loss index" was determined.

Comparative Example 2

A result when a part of the size information of the data of the SP2 was used for sorting by reanalyzing data in Comparative Example 1 was calculated and estimated. Specifically, setting to accept or reject each entire region was performed in each of the nine regions shown in FIG. 2, and a wafer including at least one defect in a rejected region was determined as a rejection target. It is to be noted that, as combinations of acceptability of the nine regions, $2^9=512$ patterns can be assumed, and a "virtual overall loss index" in each case was recalculated. A specific calculation method is as described below. A rate of the number of wafers which were determined to be rejection targets but had no void failures after SOI wafer manufacture to the total number of wafers was determined as a "virtual overkill rate", and a value provided by multiplying this rate by a material value coefficient was determined as a "virtual material loss index". On the other hand, a rate of the number of wafers which were determined to be acceptance targets but had void failures after the SOI wafer manufacture to the total number of wafers was determined as a "virtual overlooking failure rate", and a value provided by multiplying this rate by a product value coefficient was determined as a "virtual failure loss index". At last, a value provided by adding the "virtual material loss index" and the "virtual failure loss index" was determined as a "virtual overall loss index". In the assumed 512 combinations, a case where the loss becomes minimum is a case where a region "g" alone is accepted and the other eight regions are all rejected, and this was a result of Comparative Example 2.

Figure 10:
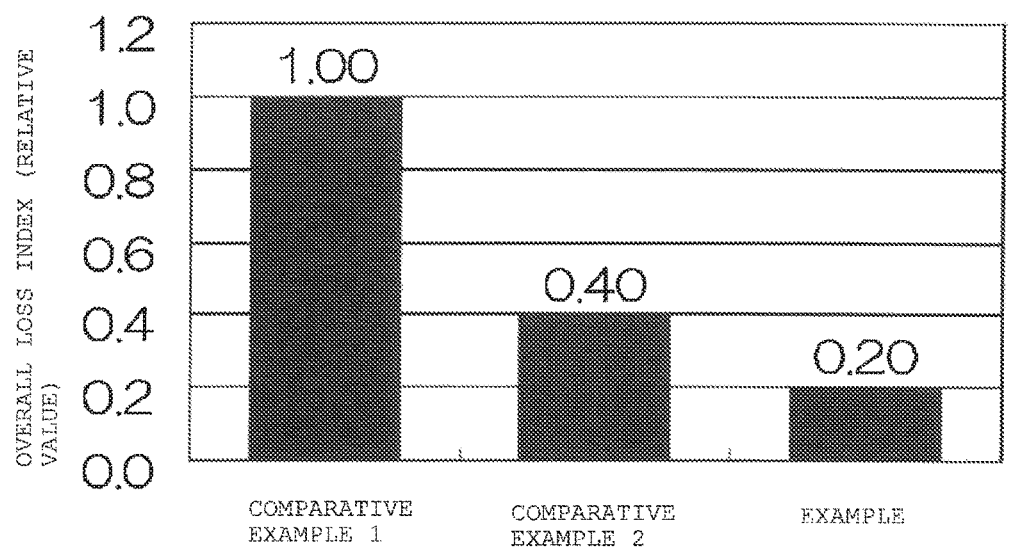
FIG. 10 is a graph comparing overall loss indexes of Example 1 and Comparative Examples 1 and 2.
Figure 11:
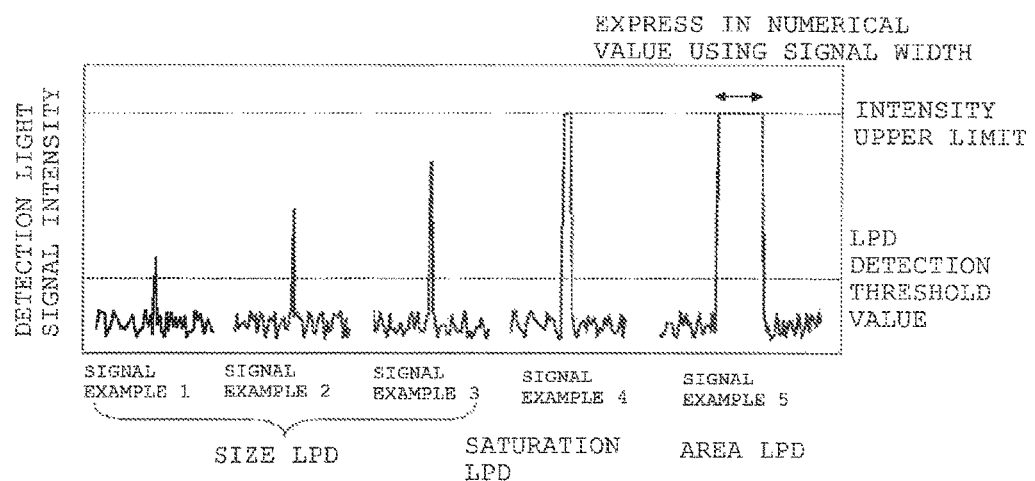
FIG. 11 is a view showing a relationship between an actual LPD size and LPD detection light signal intensity.

At last, the overall loss indexes in Example 1, Comparative Example 1, and Comparative Example 2 were compared. FIG. 10 shows a result. It is to be noted that FIG. 10 shows the respective overall loss indexes in Example 1, Comparative Example 1, and Comparative Example 2 as relative values when a value in Comparative Example 1 is determined as 1. As shown in FIG. 10, as the overall loss index in Example 1, a low result which is ⅕ of that in Comparative Example 1 and ½ of that of Comparative Example 2 was obtained, and the effectiveness of the present invention was proved.

It is to be noted that the present invention is not restricted to the embodiment. The embodiment is an illustrative example, and any example which has substantially the same structure and exerts the same functions and effects as the technical scope described in claims of the present invention is included in the technical scope of the present invention.

The invention claimed is:

1. A method for evaluating a semiconductor wafer by which LPDs on a surface of a semiconductor wafer are detected with the use of a laser surface inspection apparatus and the detected LPDs are classified into a crystal defect on the surface of the semiconductor wafer and a foreign matter on the surface of the semiconductor wafer, comprising steps of:

detecting the LPDs on the surface of a semiconductor wafer as an examination sample in two measurement modes of the laser surface inspection apparatus, the two measurement modes consisting of low-angle incidence/low-angle detection (DWO) and low-angle incidence/high-angle detection (DNO);

performing size classification based on size information of the LPDs detected in the two measurement modes;

calculating, from detection coordinates of each LPD detected in the two measurement modes, a distance between the detection coordinates and a relative angle to a wafer center in the two measurement modes;

presetting, in accordance with each classified size, determination criteria to determine each LPD having the distance between the detection coordinates and the relative angle in the two measurement modes which fall within a predetermined range as a foreign matter and to determine any LPD other than the LPD falling in the predetermined range as a killer defect which is a defect of the semiconductor wafer as an examination sample;

detecting the LPDs of a semiconductor wafer as an evaluation target in the two measurement modes;

performing size classification based on size information of the LPDs detected in the two measurement modes as to the semiconductor wafer as the evaluation target;

calculating, from detection coordinates of each LPD detected in the two measurement modes, a distance between the detection coordinates and a relative angle to a wafer center in the two measurement modes as to the semiconductor wafer as the evaluation target; and classifying the LPDs detected on a surface of the semiconductor as the evaluation target into the killer defect and the foreign matter based on a result of the calculation and the determination criteria.

2. The method for evaluating a semiconductor wafer according to claim 1,
wherein the semiconductor wafer as the examination sample and the semiconductor wafer as the evaluation target are epitaxial wafers.

3. The method for evaluating a semiconductor wafer according to claim 1,
wherein the semiconductor wafer as the evaluation target is used as a material of a silicon-on-insulator wafer.

4. The method for evaluating a semiconductor wafer according to claim 2,
wherein the semiconductor wafer as the evaluation target is used as a material of a silicon-on-insulator wafer.

5. The method for evaluating a semiconductor wafer according to claim 1,
wherein the killer defect is an epitaxial defect having a square pyramid shape.

6. The method for evaluating a semiconductor wafer according to claim 2,
wherein the killer defect is an epitaxial defect having a square pyramid shape.

7. The method for evaluating a semiconductor wafer according to claim 3,
wherein the killer defect is an epitaxial defect having a square pyramid shape.

8. The method for evaluating a semiconductor wafer according to claim 4,
wherein the killer defect is an epitaxial defect having a square pyramid shape.

9. The method for evaluating a semiconductor wafer according to claim 1,
wherein, at the time of setting the determination criteria, whether the detected LPD is the killer defect is confirmed with the use of an evaluation method different from the evaluation method using the DWO and the DNO.

10. The method for evaluating a semiconductor wafer according to claim 2,
wherein, at the time of setting the determination criteria, whether the detected LPD is the killer defect is confirmed with the use of an evaluation method different from the evaluation method using the DWO and the DNO.

11. The method for evaluating a semiconductor wafer according to claim 3,
wherein, at the time of setting the determination criteria, whether the detected LPD is the killer defect is confirmed with the use of an evaluation method different from the evaluation method using the DWO and the DNO.

12. The method for evaluating a semiconductor wafer according to claim 4,
wherein, at the time of setting the determination criteria, whether the detected LPD is the killer defect is confirmed with the use of an evaluation method different from the evaluation method using the DWO and the DNO.

13. The method for evaluating a semiconductor wafer according to claim 5,
wherein, at the time of setting the determination criteria, whether the detected LPD is the killer defect is confirmed with the use of an evaluation method different from the evaluation method using the DWO and the DNO.

14. The method for evaluating a semiconductor wafer according to claim 6,
wherein, at the time of setting the determination criteria, whether the detected LPD is the killer defect is confirmed with the use of an evaluation method different from the evaluation method using the DWO and the DNO.

15. The method for evaluating a semiconductor wafer according to claim 7,
wherein, at the time of setting the determination criteria, whether the detected LPD is the killer defect is confirmed with the use of an evaluation method different from the evaluation method using the DWO and the DNO.

16. The method for evaluating a semiconductor wafer according to claim 8,
wherein, at the time of setting the determination criteria, whether the detected LPD is the killer defect is confirmed with the use of an evaluation method different from the evaluation method using the DWO and the DNO.

* * * * *